(12) United States Patent
Sankai

(10) Patent No.: US 11,103,369 B2
(45) Date of Patent: Aug. 31, 2021

(54) ARTIFICIAL LEG MOTION ASSISTING APPARATUS AND ARTIFICIAL LEG MOTION ASSISTING METHOD

(71) Applicants: CYBERDYNE INC., Tsukuba (JP); UNIVERSITY OF TSUKUBA, Tsukuba (JP)

(72) Inventor: Yoshiyuki Sankai, Ibaraki (JP)

(73) Assignees: CYBERDYNE INC., Tsukuba (JP); UNIVERSITY OF TSUKUBA, Tsukuba (JP)

(*) Notice: Subject to any disclaimer, the term of this patent is extended or adjusted under 35 U.S.C. 154(b) by 203 days.

(21) Appl. No.: 16/462,195

(22) PCT Filed: Mar. 17, 2017

(86) PCT No.: PCT/JP2017/011071
§ 371 (c)(1),
(2) Date: May 17, 2019

(87) PCT Pub. No.: WO2018/092325
PCT Pub. Date: May 24, 2018

(65) Prior Publication Data
US 2019/0328553 A1  Oct. 31, 2019

(30) Foreign Application Priority Data
Nov. 18, 2016 (JP) ............... JP2016-225451

(51) Int. Cl.
*A61F 2/64* (2006.01)
*A61F 2/72* (2006.01)
(Continued)

(52) U.S. Cl.
CPC .......... *A61F 2/72* (2013.01); *A61F 2/64* (2013.01); *A61F 2/80* (2013.01); *A61F 2002/701* (2013.01); *A61F 2002/704* (2013.01)

(58) Field of Classification Search
CPC ...... A61F 2/72; A61F 2/64; A61F 2/80; A61F 2002/701; A61F 2002/704
See application file for complete search history.

(56) References Cited

U.S. PATENT DOCUMENTS

2004/0111163 A1  6/2004  Bedard
2006/0211956 A1*  9/2006  Sankai ............... A61F 5/0102
601/5
(Continued)

FOREIGN PATENT DOCUMENTS

JP  2006-204426 A  8/2006
JP  2010-253301 A  11/2010
(Continued)

OTHER PUBLICATIONS

International Search Report and Written Opinion for related International Application No. PCT/JP2017/011071, dated May 9, 2017; English translation of ISR provided; 11 pages.

*Primary Examiner* — Bruce E Snow
(74) *Attorney, Agent, or Firm* — Procopio, Cory, Hargreaves & Savitch LLP

(57) ABSTRACT

An artificial leg motion assisting apparatus and an artificial leg motion assisting method which are capable of transmitting knee joint motive power to a commercially-available trans-femoral prosthesis without making a wearer feel a sense of discomfort. When the artificial leg motion assisting apparatus is attached to the commercially-available trans-femoral prosthesis, a control unit controls a drive unit by a specified control method on the basis of mechanical impedance adjusted by an impedance adjustment unit and transmits output of the drive unit to a knee joint coupling.

10 Claims, 13 Drawing Sheets

(51) Int. Cl.
*A61F 2/80* (2006.01)
*A61F 2/70* (2006.01)

(56) References Cited

U.S. PATENT DOCUMENTS

| 2008/0161937 | A1 | 7/2008 | Sankai |
| 2010/0121232 | A1* | 5/2010 | Sankai ................ A61H 1/0255 601/23 |
| 2012/0259431 | A1 | 10/2012 | Han et al. |
| 2017/0119550 | A1 | 5/2017 | Sankai |

FOREIGN PATENT DOCUMENTS

| JP | 2014-144037 A | 8/2014 |
| JP | 2016-002122 A | 1/2016 |

* cited by examiner

ARTIFICIAL LEG MOTION ASSISTING APPARATUS AND ARTIFICIAL LEG MOTION ASSISTING METHOD

CROSS-REFERENCE TO RELATED APPLICATIONS

This application is a U.S. National Stage entry of PCT Application No: PCT/JP2017/011071 filed Mar. 17, 2017, which claims priority to Japanese Patent Application No. 2016-225451, filed Nov. 18, 2016, the contents of which are incorporated herein by reference.

TECHNICAL FIELD

The present invention relates to an artificial leg motion assisting apparatus and an artificial leg motion assisting method and is suited for use in a motion assisting apparatus for a wearer who wears a commercially available trans-femoral prosthesis.

BACKGROUND ART

Currently, the number of above knee amputees who had their thigh part above their knee amputated is 22,000 in Japan and 620,000 in the U.S. The above knee amputees have problems in, for example, their moving ability, social isolation, enervation, pains, sleep, and emotional disorder; and of these problems, the problem about recovery of their moving ability has very significant influence on the quality of life (QOL).

Trans-femoral prostheses are commercially available as artificial limbs to replace the amputated legs of the above knee amputees. Most types of a knee coupling substituting for a human body's knee joint, among components to compose a trans-femoral prosthesis, move passively because of properties of springs and dampers. A user of the trans-femoral prosthesis which involves such passive actions suffers limitations on movements in daily life (particularly when stepping up and down the stairs), for example, as they cannot actively perform motions to flex and extend their knee joint.

In order to overcome the above-described problem of limitations, the inventor of the present application proposes a wearable artificial limb motion assistance apparatus which makes it possible to step up and down the stairs with one leg stepping up or down each stair and smoothly switch tasks in response to the wearer's motions (see PTL 1).

However, the trans-femoral prosthesis in which an electric actuator like the wearable artificial limb motion assistance apparatus is built requires an approval of new international standards which are different from those for commercially-available trans-femoral prostheses with respect to, for example, safety tests. Therefore, it is desirable that a wearable-type motion assisting apparatus for a commercially-available trans-femoral prosthesis be made attachable (see PTL 2).

CITATION LIST

Patent Literature

PTL 1: Japanese Patent Application Laid-Open (Kokai) Publication No. 2016-2122
PTL 2: U.S. Patent Application Publication No. 2012/259431 A1

SUMMARY OF THE INVENTION

Problems to be Solved by the Invention

However, when the wearable-type motion assisting apparatus is attached to the commercially-available trans-femoral prosthesis, there is a high possibility that because a rotation axis of a knee joint coupling of the original trans-femoral prosthesis does not match a rotation axis of a joint actuator of the motion assisting apparatus, the wearer may feel a sense of discomfort when transmitting motive power from the joint actuator to the knee joint coupling.

Regarding a reinforced knee brace of PTL 2, the reinforced knee brace which performs impedance adjustment for biomimicry responses based on a walking cycle, reinforced torque, and an estimated slope can be mounted on either a human's leg part or an artificial leg; however, no consideration is paid to the weight of the apparatus itself and it is necessary to make adjustments after starting walking, so that the wearer will always feel the sense of discomfort which is felt upon the motion immediately after mounting the apparatus.

In a case of the above knee amputee, nerves do not run through their leg part at or lower than their upper thigh part. So, the problem is that the sense of discomfort given to the wearer will further increase when walking in a state where the weight of the motion assisting apparatus itself is also added.

The present invention was devised in consideration of the above-described circumstances and aims at proposing an artificial leg motion assisting apparatus and artificial leg motion assisting method capable of assisting motions without the sense of discomfort when mounted on the commercially available trans-femoral prosthesis.

Means to Solve the Problems

In order to solve the above-described problems, provided according to the present invention is a wearable-type artificial leg motion assisting apparatus which is provided separately from a trans-femoral prosthesis including a knee joint coupling for rotatably coupling a thigh socket for housing an above knee amputated end of a wearer to a lower leg support pole engaged with a foot part and which supports a rotational motion of the knee joint coupling, wherein the artificial leg motion assisting apparatus includes: a thigh frame fastened to the thigh socket via a fastening member; a lower leg frame movably retained at the lower leg support pole via a holding member; a drive unit that is coupled to the thigh frame and the lower leg frame and drives actively or passively in conjunction with a thigh motion of the wearer; a biological signal detection unit that detects an electrical potential as a biological signal generated in association with the thigh motion of the wearer; a control unit that causes the drive unit to generate motive power according to an intention of the wearer on the basis of the biological signal acquired by the biological signal detection unit; a coupling's physical amount detection unit that detects a physical amount of the knee joint coupling in association with the thigh motion of the wearer on the basis of an output signal from the drive unit; a parameter estimation unit that estimates a kinetic parameter specific to the trans-femoral prosthesis on the basis of a result of the detection measured within a specified amount of time by the coupling's physical amount detection unit; and an impedance adjustment unit that adjusts mechanical impedance specific to the knee joint coupling on the basis of the kinetic parameter estimated by the parameter estimation unit, wherein the control unit controls the drive unit by a specified control method on the basis of the mechanical impedance adjusted by the impedance adjustment unit.

When the artificial leg motion assisting apparatus is attached to the commercially-available trans-femoral prosthesis, this artificial leg motion assisting apparatus makes it possible to transmit the output of the drive unit to the knee joint coupling while eliminating the sense of discomfort felt by the wearer as much as possible even if the drive unit and the knee joint coupling of the trans-femoral prosthesis are not located at the same motive power working position.

Furthermore, according to the present invention, a leg motion monitoring unit, which is provided on the trans-femoral prosthesis and monitors a motion of a leg part where the trans-femoral prosthesis is not mounted, and the parameter estimation unit estimate the kinetic parameter of the trans-femoral prosthesis on the basis of a result of the detection by the coupling's physical amount detection unit and a result of the monitoring by the leg motion monitoring unit.

This artificial leg motion assisting apparatus makes it possible to cause the output of the drive unit to the knee joint coupling so as to eliminate the sense of discomfort felt by the wearer more accurately by referring to a walking pattern while monitoring the motion of the leg part where the trans-femoral prosthesis is not mounted.

Furthermore, according to the present invention, a sound concentrating microphone that is provided on the foot part of the trans-femoral prosthesis and collects a walking sound of the trans-femoral prosthesis is included, wherein the parameter estimation unit modifies the estimated kinetic parameter of the trans-femoral prosthesis on the basis of the walking sound collected by the sound concentrating microphone.

This artificial leg motion assisting apparatus makes it possible to transmit the output of the drive unit to the knee joint coupling so as to eliminate the sense of discomfort felt by the wearer more accurately by recognizing the state of the floor face by collecting the sound of the foot part of the trans-femoral prosthesis contacting the floor face.

Furthermore, according to the present invention, a vibration detection unit that is provided on the lower leg frame of the trans-femoral prosthesis and detects vibrations from a floor face during walking is included, wherein the parameter estimation unit modifies the estimated kinetic parameter of the trans-femoral prosthesis on the basis of the vibrations detected by the vibration detection unit.

This artificial leg motion assisting apparatus makes it possible to transmit the output of the drive unit to the knee joint coupling so as to eliminate the sense of discomfort felt by the wearer more accurately by recognizing the state of the floor face while detecting the vibrations from the floor face transmitted from the lower leg support pole of the trans-femoral prosthesis.

Furthermore, according to the present invention, the artificial leg motion assisting apparatus includes: a thigh angle sensor that is provided on the thigh frame and detects a thigh angle determined between a thigh direction and a vertical direction; a knee joint angle sensor that is provided on the drive unit and detects an angle and angular velocity of the knee joint coupling; a ground reaction force sensor that is provided on the foot part and detects a the ground reaction force to the wearer; and a data storage unit that stores a plurality of reference parameters representing a series of minimum motion units (phases) constituting motion patterns of the wearer which are classified as tasks, wherein the control unit estimates a phase of a task for the wearer by comparing the thigh angle, the knee joint angle, and the ground reaction force with the respective reference parameters stored in the data storage unit and then causes the drive unit to generate motive power according to the estimated phase.

This artificial leg motion assisting apparatus makes it possible to walk in a manner similar to a healthy person by estimating the phase of the wearer's task and switching the task smoothly in response to the wearer's motion, that is, not only walking on level ground, but also stair stepping motions, while causing the drive unit to generate the motive power according to the relevant phase.

Furthermore, provided according to the present invention is a wearable-type artificial leg motion assisting method by a wearable-type artificial leg motion assistance which is provided separately from a trans-femoral prosthesis including a knee joint coupling for rotatably coupling a thigh socket for housing an above knee amputated end of a wearer to a lower leg support pole engaged with a foot part and which supports a rotational motion of the knee joint coupling, wherein the artificial leg motion assisting method includes: a first step of detecting an electrical potential as a biological signal generated in association with a thigh motion of the wearer; a second step of causing a drive unit to generate motive power according to an intention of the wearer on the basis of the biological signal acquired in the first step; a third step of detecting a physical amount of the knee joint coupling in association with the thigh motion of the wearer on the basis of an output signal from the drive unit which is coupled to a thigh frame fastened to the thigh socket via a fastening member and a lower leg frame movably retained at the lower leg support pole via a holding member and which drives actively or passively in conjunction with the thigh motion of the wearer; a fourth step of estimating a kinetic parameter specific to the trans-femoral prosthesis on the basis of a result of the detection measured within a specified amount of time in the third step; a fifth step of adjusting mechanical impedance specific to the knee joint coupling on the basis of the kinetic parameter estimated in the fourth step; and a sixth step of controlling the drive unit by a specified control method on the basis of the mechanical impedance adjusted in the fifth step.

When the artificial leg motion assisting apparatus is attached to the commercially-available trans-femoral prosthesis, this artificial leg motion assisting method makes it possible to transmit the output of the drive unit to the knee joint coupling while eliminating the sense of discomfort felt by the wearer as much as possible even if the drive unit and the knee joint coupling of the trans-femoral prosthesis are not located at the same motive power working position.

Advantageous Effects of the Invention

The artificial leg motion assisting apparatus and artificial leg motion assisting method capable of transmitting the knee joint motive power to the commercially-available trans-femoral prosthesis without causing the wearer to feel the sense of discomfort can be implemented according to the present invention.

DESCRIPTION OF EMBODIMENTS

An embodiment of the present invention will be described below in detail with reference to the drawings.

Figure 1:
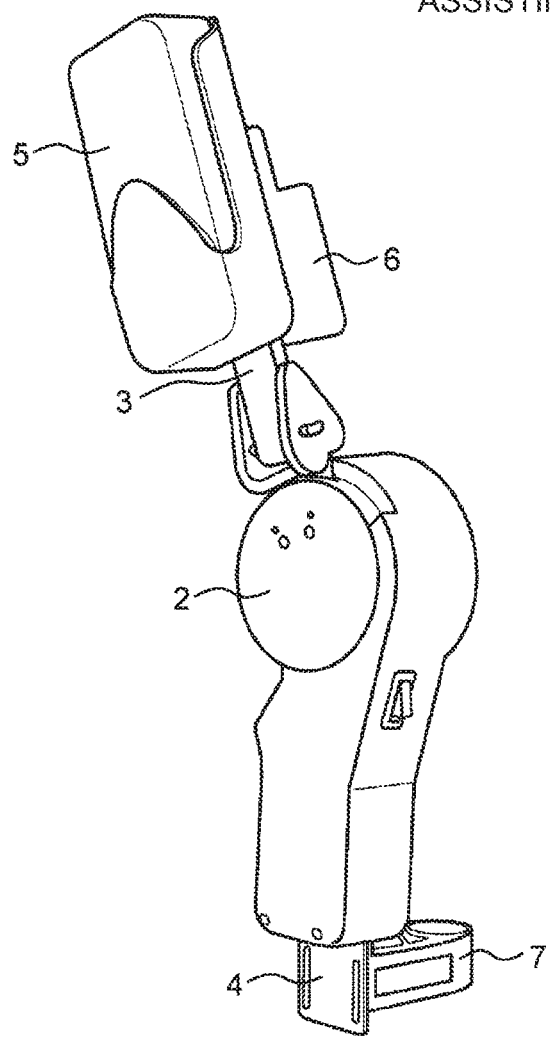
FIG. 1 is an outside drawing illustrating an overall configuration of an artificial leg motion assisting apparatus according to an embodiment of the present invention.
Figure 1:

(1) Configuration of Artificial Leg Motion Assisting Apparatus According to this Embodiment FIG. 1 illustrates a wearable-type artificial leg motion assisting apparatus 1 according to this embodiment; and a thigh frame 3 and a lower leg frame 4 are coupled to one end and the other end of a driving unit (drive unit) 2, in which an actuator is built, respectively, and the thigh frame 3 and the lower leg frame 4 are movable relatively to each other around a drive shaft of the actuator as a rotation center.

The thigh frame 3 and the lower leg frame 4 have frame bodies which are formed to have long plate shapes made of metal such as stainless steel or carbon fibers and are designed to be light-weighted and have high rigidity.

Furthermore, a control apparatus 5 (FIG. 4) for controlling driving of the actuator and a power supply battery (not shown) are attached to the outside of the thigh frame 3 and a thigh socket cuff (fastening member) 6 is connected to the inside of the thigh frame 3. A lower leg connection ring (holding member) 7 is connected to the inside lower end of a frame body of the lower leg frame 4.

This driving unit 2 is equipped with a group of many types of sensors and is designed to be capable of executing corresponding various motions based on each piece of sensor information. Furthermore, the artificial leg motion assisting apparatus 1 is equipped with an insole 8 which is to be mounted in a foot part of the trans-femoral prosthesis described below and is provided separately from the driving unit 2 and so on.

Figure 2:
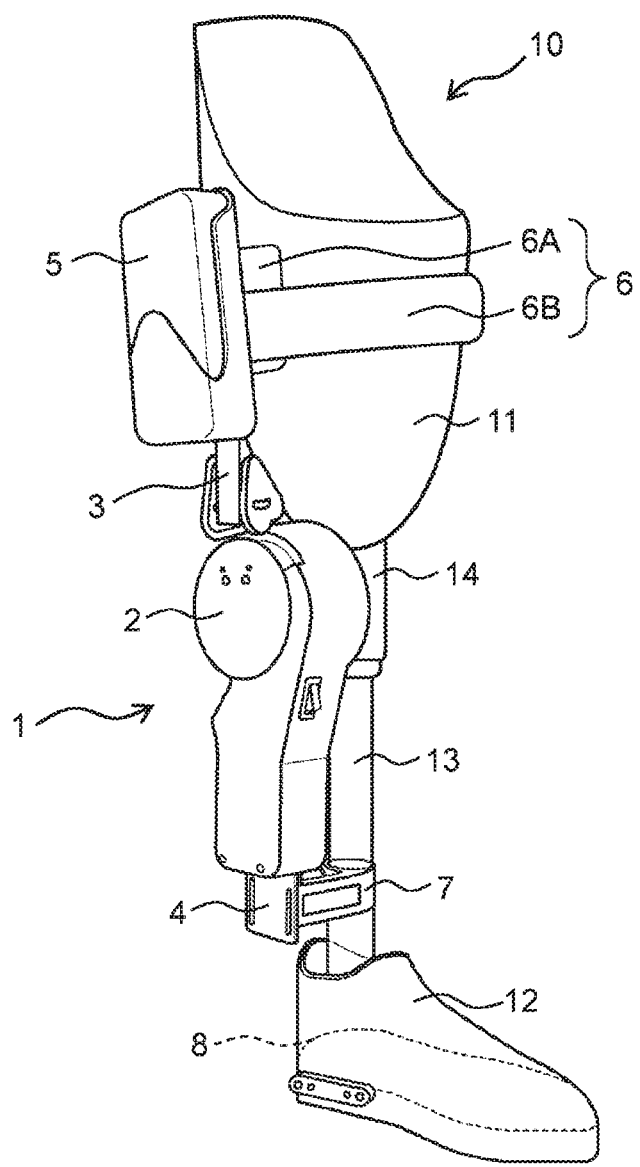
FIG. 2 is a perspective view illustrating an outside configuration of the artificial leg motion assisting apparatus mounted on a trans-femoral prosthesis according to an embodiment of the present invention.

FIG. 2 illustrates a state where the artificial leg motion assisting apparatus 1 according to the present invention is attached to a commercially-available trans-femoral prosthesis. A commercially-available trans-femoral prosthesis 10 in this embodiment includes a knee joint coupling 14 for rotatably coupling a thigh socket 11 for housing the wearer's above knee amputated end to a lower leg support pole 13 which engages with a foot part 12.

When the artificial leg motion assisting apparatus 1 according to the present invention is attached to the trans-femoral prosthesis 10, the thigh frame 3 is secured and connected to the thigh socket 11 by winding and firmly fastening the thigh socket cuff 6 around and to the thigh socket 11, and the lower leg frame 4 is retained in a manner such that it can slide and move relative to the lower leg support pole 13 along a lengthwise direction of the lower leg support pole, by winding the lower leg connection ring 7 not so tightly around a lower part (a site corresponding to an ankle) of the lower leg support pole 13.

Accordingly, while the thigh frame 3 is secured to the thigh socket 11, the lower leg frame 4 is retained loosely relative to the lower leg support pole 13; and, therefore the drive power of the actuator for the driving unit 2 can be reflected as rotational power of the knee joint coupling 14.

If the lower leg frame 4 were secured to the lower leg support pole 13, the rotation axis of the actuator for the driving unit 2 does not match that of the knee joint coupling 14 and, therefore, there would be a high possibility that the actuator for the drive unit might enter the state of being locked. Consequently, an error in the above-mentioned rotation axis can be absorbed by sliding the lower leg frame 4 relative to the lower leg support pole 13.

Figure 3:
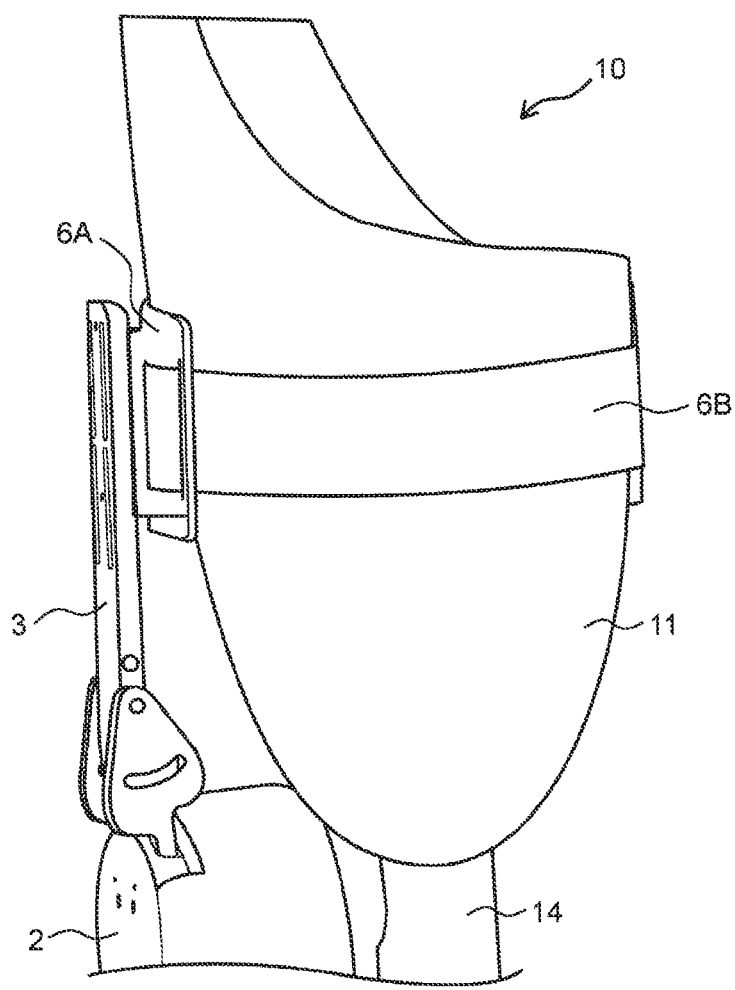
FIG. 3 is a fragmentary enlarged view for explaining a fastened state of a thigh socket and a thigh frame.

Incidentally, as illustrated in FIG. 3, the thigh socket cuff 6 has a double structure of a wide hardened fastening belt 6A and a flexible band 6B whose width is narrower than that of the hardened fastening belt 6A; and the entire thigh socket 11 and the thigh frame 3 can be firmly fastened to each other, regardless the type of the thigh socket 11, by firstly firmly winding the hardened fastening belt 6A around the thigh socket 11 and further winding the flexible band 6B by using the hardened fastening belt 6A as a base.

(2) Internal System Configuration of Artificial Leg Motion Assisting Apparatus 1

Figure 4:
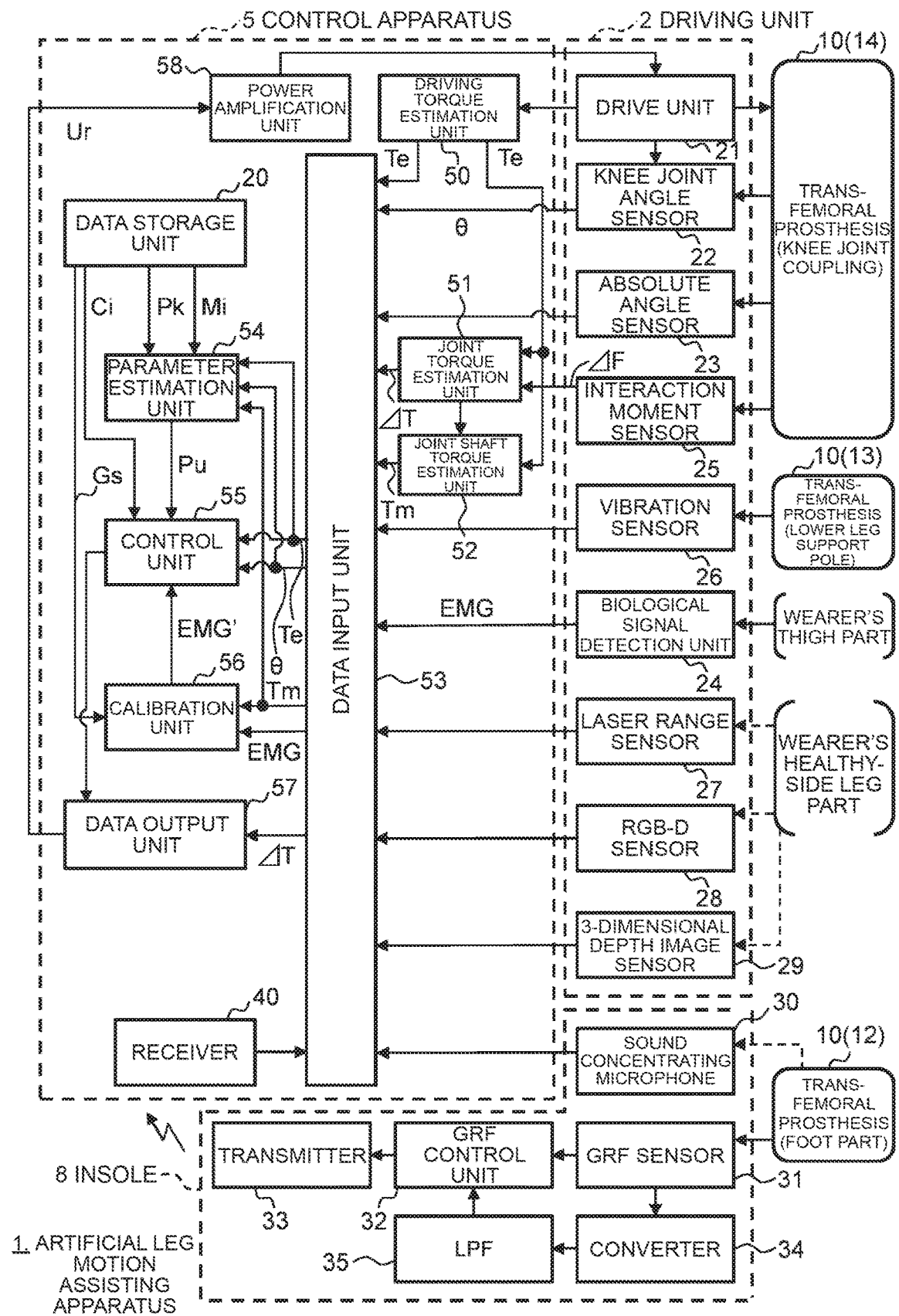
FIG. 4 is a block diagram illustrating the configuration of a control system for the artificial leg motion assisting apparatus according to an embodiment of the present invention.

FIG. 4 illustrates the configuration of a control system for the artificial leg motion assisting apparatus 1 according to this embodiment. The control system: is mainly built in the control apparatus 5 which performs integrated control of the entire apparatus; and has a data storage unit 20 from and to which various kinds of data can be read and written in accordance with commands from the control apparatus 5 and in which the various kinds of data are formed into a database.

The driving unit 2 connected to the control apparatus 5 has: a drive unit 21 including an actuator which applies an assist force to the wearer's trans-femoral prosthesis 10; and a group of various kinds of sensors. The assist force herein used means power which generates torque acting with the knee joint coupling 14 of the trans-femoral prosthesis 10 as the rotation axis.

The driving unit 2 is provided with a knee joint angle sensor 22, which is composed of a potentiometer for detecting a rotation angle of an output shaft of the actuator for the drive unit 21, coaxially with the output shaft of the actuator for the drive unit 21 and is designed to detect a knee joint angle and an angular velocity in response to the wearer's motion.

An absolute angle sensor 23 is composed of an acceleration sensor and a gyrosensor, which are provided on the thigh frame 3, and measures an absolute angle of the lower leg frame 4 relative to the thigh frame 3 around the output shaft of the actuator as the rotation center (a thigh angle determined between a thigh direction and a vertical direction).

Furthermore, a biological signal detection unit 24 which is composed of a biological signal detection sensor is located on a body surface at a position near the wearer's above knee amputated end and is designed to detect a biological potential signal (for example, surface myogenic potential [EMG: Electro Myogram/Myoelectricity] which is generated by a command signal from the upper central nervous system in a form of an electrical potential on a muscle surface via the spinal cord) for causing the knee joint coupling 14 of the relevant wearer's trans-femoral prosthesis 10 to operate.

An interaction moment sensor 25 is composed of a strain gauge adhered to a connecting part between the actuator and the lower leg frame 4 and measures a moment of force which acts between the actuator and the lower leg support pole 13 for the trans-femoral prosthesis 10 on the basis of strain of the lower leg frame 4. This measurement result becomes a criterion representing an exercise load by the driving unit 2 and simultaneously representing a torque transmission level from the actuator during the motion assist.

The lower leg frame 4 for the trans-femoral prosthesis 10 is provided with a vibration sensor 26, which is composed of a piezoelectric-type acceleration sensor, and detects slight vibrations applied from the floor face during walking via the foot part 12 of the trans-femoral prosthesis 10 to the lower leg support pole 13.

Furthermore, the driving unit 2 is equipped with a laser range sensor 27, an RGB-D sensor 28, and a 3-dimensional depth image sensor 29 as a leg motion monitoring unit, which is designed to monitor motions of the leg part on the side where the trans-femoral prosthesis 10 is not mounted.

The laser range sensor 27 illuminates an object (obstacle), as seen from an installed position, with light and calculates the distance by receiving its reflected light. By measuring this distance at certain angle intervals, fan-shaped distance information can be obtained within the range of a maximum distance of 30 m at an angle of 240 degrees on a plane surface.

The RGB-D sensor 28 has, in addition to an RGB color camera function, a depth sensor capable of measuring the distance to the object (obstacle) as seen from the camera and can perform 3-dimensional scanning of the object. This depth sensor is composed of an infrared sensor, captures images of the object in a state of projecting a single pattern of structured light on the object and calculates the depth of each point on the images by means of triangulation by using its parameter.

For example, when Kinect (a trade name of Microsoft) is applied as the RGB-D sensor 28, it is possible to capture images within the range of a horizontal visual field of 57 degrees, a vertical visual field of 43 degrees, and a sensor range of 1.2 m to 3.5 m and both RGB images of 640×480 pixels and depth images of 320×240 pixels can be obtained at 30 frames/second.

The 3-dimensional depth image sensor 29 calculates information about the distance to the object in pixel units by illuminating the object with LED pulses and measuring the time required for the reflected light to reach from the object in pixel units and, at the same time, superimposing the acquired image information. This 3-dimensional depth image sensor 29 has detection capability with higher accuracy than that of the above-mentioned RGB-D sensor 28 and has a wider view angle than that of the laser range sensor 27, so that the 3-dimensional depth image sensor 29 is useful as a complementary sensor. For example, when Pixel Soleil (a product name of NIPPON SIGNAL CO., LTD.) is applied as the 3-dimensional depth image sensor 29, it is possible to capture images within the range of a horizontal visual field of 72 degrees, a vertical visual field of 72 degrees, and a sensor range of 0.3 m to 4.0 m.

Moreover, the insole 8 (FIG. 1) mounted in the foot part 12 of the trans-femoral prosthesis 10 is provided with a sound concentrating microphone 30 and is thereby designed to collect walking sound of the trans-femoral prosthesis 10.

This insole 8 is provided with a GRF (Ground Reaction Force) sensor 31 at a position corresponding to a foot sole in the foot part 12 of the trans-femoral prosthesis 10 and detects a reaction force to the load imposed on a foot sole surface of the foot part 12 mounted on the wearer's trans-femoral prosthesis 10 (that is, the ground reaction force). This GRF sensor 31 can measure the load imposed on the foot sole surface by dividing it into a front foot part (toe part) and a rear foot part (heel part) and measuring the load on the respective divided foot parts independently.

This GRF sensor 31: is composed of, for example, a piezoelectric element which outputs a voltage according to the applied load or a sensor whose electrostatic capacity changes according to the load; and can detect changes in the load as caused by movements of the body weight and whether the wearer's leg is in contact with the ground or not.

The insole 8 mounted in the foot part 12 includes, other than the sound concentrating sensor 30 and the GRF sensor 31, a GRF control unit 32 which is composed of an MCU (Micro Control Unit), and a transmitter 33. After output from the GRF sensor 31 is converted into a voltage via a converter 34, a high frequency band is blocked via an LPF (Low Pass Filter) 35 and then the obtained result is input into the GRF control unit 32.

This GRF control unit 32: finds changes in the load as caused by movements of the wearer's body weight and whether the wearer's leg is in contact with the ground or not, on the basis of the detection result of the GRF sensor 31; and wirelessly transmits this as GRF data via the transmitter 33 to a receiver 40 in the control apparatus 5.

The control apparatus 5 includes a driving torque estimation unit 50, a joint torque estimation unit 51, a joint shaft torque estimation unit 52, a data input unit 53, the data storage unit 20, a parameter estimation unit 54, a control unit 55, a calibration unit 56, a data output unit 57, and a power amplification unit 58.

The driving torque estimation unit 50 estimates driving torque (Te) generated by the drive unit (actuator) 21. For example, the estimation of the driving torque (Te) can be applied by detecting a current value supplied to the drive unit 21 and multiplying this current value by a torque constant which is specific to the drive unit 21.

The joint torque estimation unit 51 estimates a joint moment ($\Delta T$) of the knee joint coupling 14 for the trans-femoral prosthesis 10 from the difference between the result of multiplication of a relative force ($\Delta F$), which is detected by the relative action moment sensor 25, by a preset coefficient and the estimated driving torque value (Te). Since a combined force of the driving torque (Te) of the drive unit 21 and joint shaft torque (Tm) of the knee joint coupling 14 acts, as a joint moment ($\Delta T$), on the trans-femoral prosthesis 10, this enables the wearer to operate the trans-femoral prosthesis 10 with smaller muscle power than a case where the artificial leg motion assisting apparatus 1 is not mounted.

The joint shaft torque estimation unit 52 estimates the joint shaft torque (Tm) of the knee joint coupling 14 which is caused by the wearer's muscle power on the basis of the estimated driving torque value (Te) estimated by the driving torque estimation unit 50 and the estimated joint moment value (ΔT) estimated by the joint torque estimation unit 51. Incidentally, the joint shaft torque (Tm) is to be found in order to enable parameter estimation even under the circumstance where the wearer generates the muscle power; and it is advantageous to do so when the parameter estimation is conducted in the wearer's motion state.

The data input unit 53 is an input interface for detected data from various kinds of detection units and estimated data from various kinds of estimation units in the artificial leg motion assisting apparatus 1. Output information from the knee joint angle sensor 22, the absolute angle sensor 23, the biological signal detection unit 24, the relative action moment sensor 25, the GRF sensor 31, the vibration sensor 26, the laser range sensor 27, the RGB-D sensor 28, and the 3-dimensional depth image sensor 29 in the driving unit 2 is input to this data input unit 53.

The data storage unit 20 stores necessary data for executing various arithmetic processing in the control apparatus 5.

The parameter estimation unit 54: configures a target motion equation in an arithmetic environment by using motion equation data (Mi) and known parameters (Pk) which are read from the data storage unit 20; and is configured so that the estimated driving torque value (Te), the estimated joint torque value (ΔT), and the joint angle θ from the data input unit 53 can be substituted in the motion equation.

The motion equation data (Mi) herein used constitutes the motion equation for the entire system composed of the wearer including the artificial leg motion assisting apparatus 1 and the trans-femoral prosthesis 10, while the known parameters (Pk) are composed of the weight of each units for the artificial leg motion assisting apparatus 1 and kinetic parameters such as an inertia moment, viscosity coefficient, and Coulomb's friction coefficient of the knee joint coupling 14.

The parameter estimation unit 54 executes arithmetic processing in consideration of the estimated driving torque data (T'), the joint data (θ), and the joint moment value (ΔT) which have been read, and even the joint shaft torque (Tm), estimates unknown kinetic parameters (Pu) such as the weight of each unit for the trans-femoral prosthesis 10 and the inertia moment, the viscosity coefficient, and the Coulomb's friction coefficient of the knee joint coupling 14, repeats the estimation more than once (for example, 10 times) to average the values, and sends the obtained values to the control unit 55.

The calibration unit 56 reads a ratio of the estimated joint shaft torque (Tm) to myogenic potential (EMG) from the data input unit 53 (Tm/EMG) and a specified set gain (Gs) from the data storage unit 20; and if the set gain (Gs) is out of an allowable error range (Ea), the calibration unit 56 finds corrected myogenic potential data (EMG') by correcting the myogenic potential data (EMG) in order to make a ratio of the joint shaft torque (Tm) to the corrected myogenic potential (EMG') (Tm/EMG') substantially equal to the set gain (Gs).

As a result, it is possible to prevent the situation where estimation accuracy of the unknown kinetic parameters (Pu) of the trans-femoral prosthesis 10 degrades and to also prevent the situation where the assist force generated by the drive unit 21 becomes excessively small or large.

The control unit 55 is configured to be capable of reading control method data (Ci) from the data storage unit 20, the estimated driving torque value (Te), the estimated joint torque value (ΔT), and the joint angle θ from the data input unit 53, the estimation parameter (Pi) from the parameter estimation unit 54, and the corrected myogenic potential (EMG') from the calibration unit 56.

Furthermore, the control unit 55 configures a specified control unit in the arithmetic environment by using the control method data (Ci) and is capable of sending a control signal (Ur) for controlling driving of the drive unit 12 by reflecting the estimated driving torque value (Te), the estimated joint torque value (ΔT), the joint angle θ, the estimation parameter (Pi), and the myogenic potential (EMG') in this control unit.

The data output unit 57 is an output interface for sending the control signal (Ur) from the control unit 55 to the power amplification unit 58. The power amplification unit 58 drives the drive unit 21 in response to the control signal Ur from the data output unit 57.

Furthermore, the artificial leg motion assisting apparatus 1 is designed to control the assist force based on the impedance adjustment in order to solve natural control interference attributable to restrictions by physical properties of the apparatus itself, that is, viscoelasticity of the knee joint coupling 14 for the trans-femoral prosthesis 10 and inertia of the frames.

Specifically speaking, with the artificial leg motion assisting apparatus 1, the control unit (impedance adjustment unit) 55 adjusts the mechanical impedance specific to the knee joint coupling 14 on the basis of the kinetic parameters which are specific to the trans-femoral prosthesis 10 and are estimated according to the detection results of the coupling's physical amount detection unit (the knee joint angle sensor 22, the absolute angle sensor 23, and the relative action moment sensor 25); and the inertia moment, viscosity, and elasticity of the knee joint coupling 14 for the trans-femoral prosthesis 10 are compensated and an assist rate in the walking motion is enhanced by controlling the drive unit (actuator) 21 based on the mechanical impedance; and the sense of discomfort felt by the wearer who wears the trans-femoral prosthesis 10 can be reduced.

Accordingly, the artificial leg motion assisting apparatus 1 can indirectly change and adjust the properties of the trans-femoral prosthesis 10 by changing the properties of the entire system where the trans-femoral prosthesis 10 is added to the apparatus itself. For example, by adjusting the driving torque so as to suppress influence of an inertia term and a viscosity friction term on the entire system, the wearer can exercise their ability, which they originally have, at maximum to perform prompt motions such as reflexes. Furthermore, it is also possible to suppress the influence of the inertia term and the viscosity friction term on the trans-femoral prosthesis 10 itself and cause the wearer to walk faster than their original cycle or perform motions more smoothly (with less viscous friction) than before wearing the trans-femoral prosthesis 10.

Furthermore, the artificial leg motion assisting apparatus 1 in the state of being mounted on the wearer's trans-femoral prosthesis 10 can have the parameter estimation unit 54 estimate the kinetic parameters specific to the wearer and have the control apparatus 5 control the drive unit 21 on the basis of the motion equation in which the estimated kinetic parameters are substituted, so that the artificial leg motion assisting apparatus 1 can exert effects according to the control method used by the control apparatus 5 regardless of variation factors such as the type of the trans-femoral prosthesis 10 and individual differences.

Furthermore, the drive unit 21 can be controlled by the control apparatus 5 according to the motion equation in which the joint shaft torque (Tm) estimated by the joint shaft torque estimation unit 52 is also substituted, so that the kinetic parameters can be estimated even in the state where the muscle power is generated from the wearer; and the above-described effects can be exerted without requiring the wearer to suffer wait time to estimate the kinetic parameters.

The calibration unit 56 is further included, which adjusts mutual gain between the myogenic potential (EMG) detected by the biological signal detection unit 24 and the joint shaft torque (Tm) detected by the joint shaft torque estimation unit 52 so that the mutual gain becomes the set gain (Gs) which is set in advance. So, it is possible to prevent the situation where defective sensibility or excessive sensibility may occur in the detection result from the biological signal detection unit 24.

As a result, it is possible to prevent the situation where the kinetic parameter estimation accuracy of the trans-femoral prosthesis 10 may degrade; and it is also possible to prevent the situation where the assist force generated by the drive unit 21 may become excessively small or large. Additionally, the artificial leg motion assisting apparatus 1 according to this embodiment can perform the calibration even in the state where the muscle power is generated from the wearer who wears the trans-femoral prosthesis 10; and the wearer is not required to suffer wait time to perform the calibration.

Since the drive unit can be controlled by applying at least either one of gravity compensation or inertia compensation using the kinetic parameters estimated by the parameter estimation unit 54 to the control apparatus 5 and thereby adjusting the mechanical impedance specific to the knee joint coupling 14, it is possible to prevent: the situation where the weight of the apparatus itself may become a burden to the wearer, and the situation where the inertia of the apparatus itself may give the sense of discomfort to the wearer while in motion.

Consequently, regarding the artificial leg motion assisting apparatus according to this embodiment, even if the drive unit and the knee joint coupling for the trans-femoral prosthesis are not located at the same motive power working position when the artificial leg motion assisting apparatus is attached to the commercially-available trans-femoral prosthesis, it is possible to transmit the output of the drive unit to the knee joint coupling while eliminating the sense of discomfort felt by the wearer as much as possible.

Incidentally, the control apparatus 5 is designed so that the GRF data which is the detection result of the GRF sensor 31 mounted in the insole 8 is wirelessly transmitted from the transmitter 33 in the insole 8 and is received by the data input unit 53 via the receiver 40. After receiving the GRF data which is input to the data input unit 53, the control unit 55 stores the load, which is imposed on the foot sole based on the GRF data, in the data storage unit 20.

Furthermore, the control apparatus 5 is designed so that as the parameter estimation unit 54 estimates the kinetic parameters of the trans-femoral prosthesis 10 on the basis of the detection results of the coupling's physical amount detection unit (the knee joint angle sensor 22, the absolute angle sensor 23, and the relative action moment sensor 25) and the monitoring results of the leg motion monitoring unit (the laser range sensor 27, the RGB-D sensor 28, and the 3-dimensional depth image sensor 29), it becomes possible to transmit the output of the drive unit 21 to the knee joint coupling 14 so as to eliminate the sense of discomfort felt by the wearer more accurately by referring to the walking pattern while also monitoring the motions of the leg part where the trans-femoral prosthesis 10 is not mounted.

Furthermore, the control apparatus 5 is designed so that as the parameter estimation unit 54 modifies the estimated kinetic parameters of the trans-femoral prosthesis 10 while recognizing the state of the floor face on the basis of the walking sound of the trans-femoral prosthesis 10 which is collected by the sound concentrating microphone 30, it becomes possible to transmit the output of the drive unit 21 to the knee joint coupling 14 so as to eliminate the sense of discomfort felt by the wearer more accurately.

Furthermore, the control apparatus 5 is configured so that as the parameter estimation unit 54 modifies the estimated kinetic parameters of the trans-femoral prosthesis 10 while recognizing the state of the floor face on the basis of the vibrations detected by the vibration sensor (vibration detection unit) 26, it becomes possible to transmit the output of the drive unit 21 to the knee joint coupling 14 so as to eliminate the sense of discomfort felt by the wearer more accurately.

(3) Assist Control Associated with Wearer's Walking Motion

Next, an explanation will be provided about the assist control executed by the control apparatus 5 in association with the wearer's walking motion when the artificial leg motion assisting apparatus 1 is mounted on the wearer's trans-femoral prosthesis 10.

The artificial leg motion assisting apparatus 1 according to this embodiment is configured so that the control apparatus 5 controls the driving unit 2 by applying a different control method to each phase by executing phase sequence control described later.

The data storage unit 20 for the control apparatus 5 stores a plurality of reference parameters representing a series of minimum motion units (phases) which constitute the wearer's motion patterns classified as tasks.

The control unit 55 estimates a phase of the wearer's task by comparing the thigh angle detected by the absolute angle sensor 23, the knee joint angle data detected by the knee joint angle sensor (potentiometer) 22, and the load data detected by the GRF sensor 31 with the knee joint angle and the load which are the reference parameters stored in the data storage unit 20.

Then, the control unit 55 generates a command signal according to control data of the specified phase and supplies a command signal for causing the drive unit 21 to generate this motive power to the power amplification unit 58. The power amplification unit 58 controls the size and rotation angle of torque of the actuator by controlling the electric current to drive the actuator for the drive unit 21 and thereby assigns the assist force by the actuator to the knee joint coupling 14 of the trans-femoral prosthesis 10.

Accordingly, the artificial leg motion assisting apparatus 1 is designed so that the control signal for controlling the actuator is amplified by the power amplification unit 58 on the basis of a detection signal detected by the biological signal detection unit (biological signal detection sensor) 24, which is pasted on the wearer's thigh part, and the amplified control signal is supplied to the actuator for the drive unit 21, and the torque of the actuator is transmitted as the assist force to the knee joint coupling 14 of the trans-femoral prosthesis 10.

In a case of a healthy person under this circumstance, basic walking patterns are generated in the brain stem and the spinal cord, so that the person can walk almost automatically without being conscious of motions of their arms and legs. Therefore, the wearer who uses the artificial leg motion assisting apparatus 1 also needs to be able to walk almost automatically. For this purpose, motion assistance is provided during walking by performing autonomous walking control to control the driving unit 2 which estimates the walking state.

Consequently, in this embodiment, the control apparatus 5 controls the driving unit 2 based on the measurement result by the GRF sensor 31 by recognizing the walking state by dividing it into phases of a swing leg period and a stance leg period. The swing leg period is a period of the motion when the relevant foot moves away from the ground and the lower leg is swung forwards. The stance leg period is a period when the foot contacts the ground and supports the person's own weight.

Figure 5:
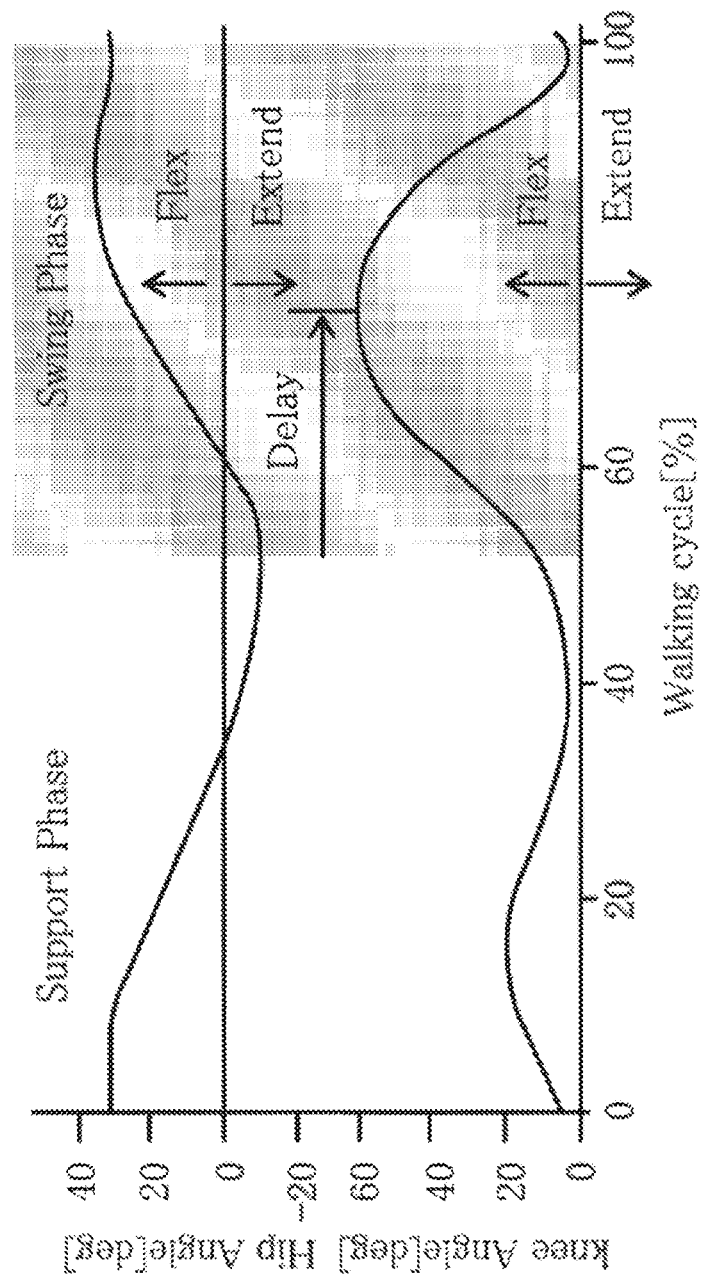
FIG. 5 is a diagram illustrating the relationship between a hip joint angle of a thigh part and a knee joint angle of a knee joint coupling 14 for a trans-femoral prosthesis 10 while walking.

FIG. 5 illustrates a hip joint angle of the wear's thigh part and a knee joint angle of the knee joint coupling 14 for the trans-femoral prosthesis 10 while walking. The knee joint coupling 14 is flexed immediately after the transition is made from the stance leg period to the swing leg period. At the same time, the hip joint is flexed and the foot moves forwards. From the middle of the swing leg period, the knee joint starts to extend behind the hip join flexion timing.

So, regarding the swing leg period control, the angular velocity is calculated from the thigh angle obtained from the absolute angle sensor 23 so that the lower leg support pole 13 of the trans-femoral prosthesis 10 follows the motion of the thigh part in a delayed manner and the drive unit 21 is controlled by using the angular velocity so that the knee joint coupling 14 is flexed in conjunction with the hip joint. During the stance leg period, position control is performed by setting a completely extended position as a target angle in order to prevent buckling of the knee joint coupling 14.

Figure 6:
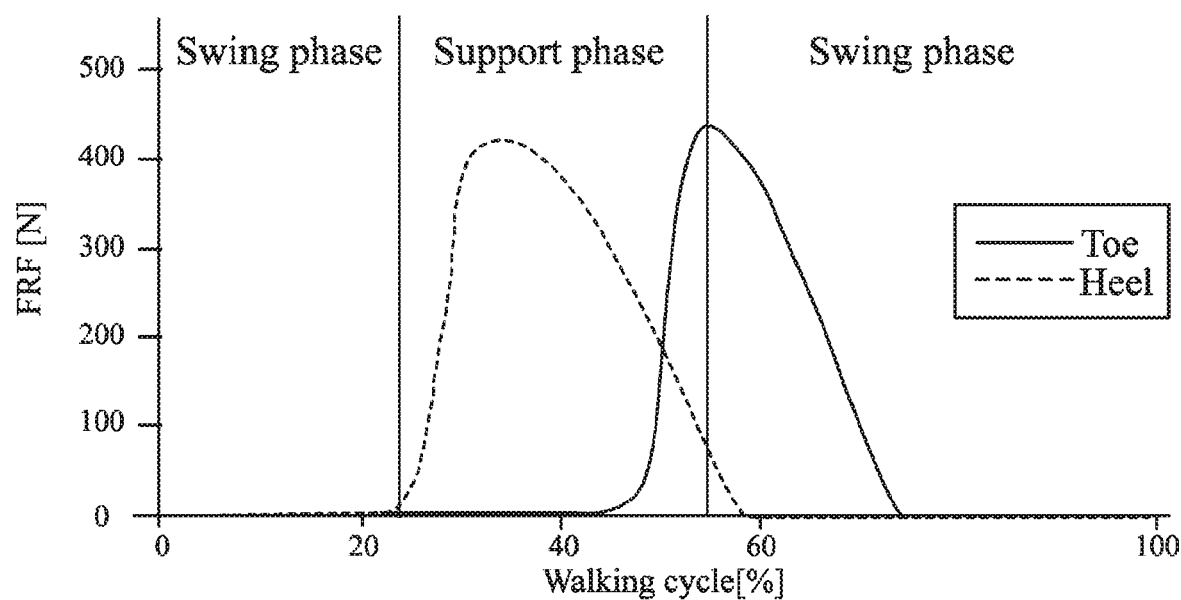
FIG. 6 is a diagram illustrating a ground reaction force while walking.

In order to switch the control between the swing leg period and the stance leg period, the control unit 55 needs to judge the phase. FIG. 6 indicates the ground reaction force on the front foot part (toe part) and the rear foot part (heel part), respectively, while walking. Since the foot part 12 contacts the ground from its rear foot part (heel part) while walking, the ground reaction force on the rear foot part side increases ahead of the ground reaction force on the front foot part (toe part) side. When the foot moves away from the floor, the rear foot part of the foot part 12 firstly moves away from the floor and then the front foot part moves away from the floor. So, the ground reaction force on the front foot part side decreases later than the ground reaction force on the rear foot part side.

By using these, the control unit 55 judges the phase based on information about the ground reaction force on the front foot part side and the ground reaction force on the rear foot part side in the insole 8 (the GRF data representing the load). When the ground reaction force on the rear foot part side increases, it is determined to switch the swing leg period to the stance leg period; and when the ground reaction force on the front foot part side decreases, it is determined to switch the stance leg period to the swing leg period.

In an actual environment, for example, obstacles may sometimes exist along a walking route. So, there may be a situation where it becomes necessary to switch to voluntary movements during autonomous walking control. Then, hybrid control of the autonomous walking control and the voluntary movement control is performed. The control of the stance leg period is prioritized than the voluntary movement control and is switched to the voluntary movement control only when the intention of motion motions is detected during the swing leg period. As a result, it is possible to avoid obstacles along the walking route.

Regarding the voluntary movement control, the driving unit 2 is controlled by detecting the intention of motion via the biological potential signal. Regarding the biological signal detection unit 24, the biological signal detection sensor is pasted at two positions on the thigh where the surface myogenic potential on the flexed side and the extended side of the knee joint can be detected; and the intention of motion is estimated from the difference in the strength of the biological potential signal. The flexion and the extension are respectively recognized as phases.

(3-1) Control Method for Stepping Up Stairs

The different phases of the swing leg period and the stance leg period are used in order to step up stairs. When the foot part 12 of the trans-femoral prosthesis 10 touches the stair, the front foot part (toe part) side firstly touches the stair before the rear foot part (heel part) side. When the ground reaction force on the front foot part side increases, the phase makes the transition from the swing leg period to the stance leg period.

When the foot part 12 moves away from the stair, the rear foot part side firstly moves away from the stair before the front foot part side. When the ground reaction force on the rear foot part side decreases, the phase makes the transition from the stance leg period to the swing leg period.

During the stance leg period, torque is calculated by using the relationship determined between the knee joint angle and the torque of a healthy person as an example. In this embodiment, torque $\tau$ is expressed as the following formula (1).

[Math. 1]

$$\mathcal{T} = \begin{cases} \alpha \theta_k + \beta & (\theta_k \leq \theta_{t1}) \\ -\alpha' \theta_k + \beta' & (\theta_{t1} < \theta_k \leq \theta_{t2}) \\ \beta'' & (\theta_{t2} < \theta_k) \end{cases} \quad (1)$$

Figure 7:
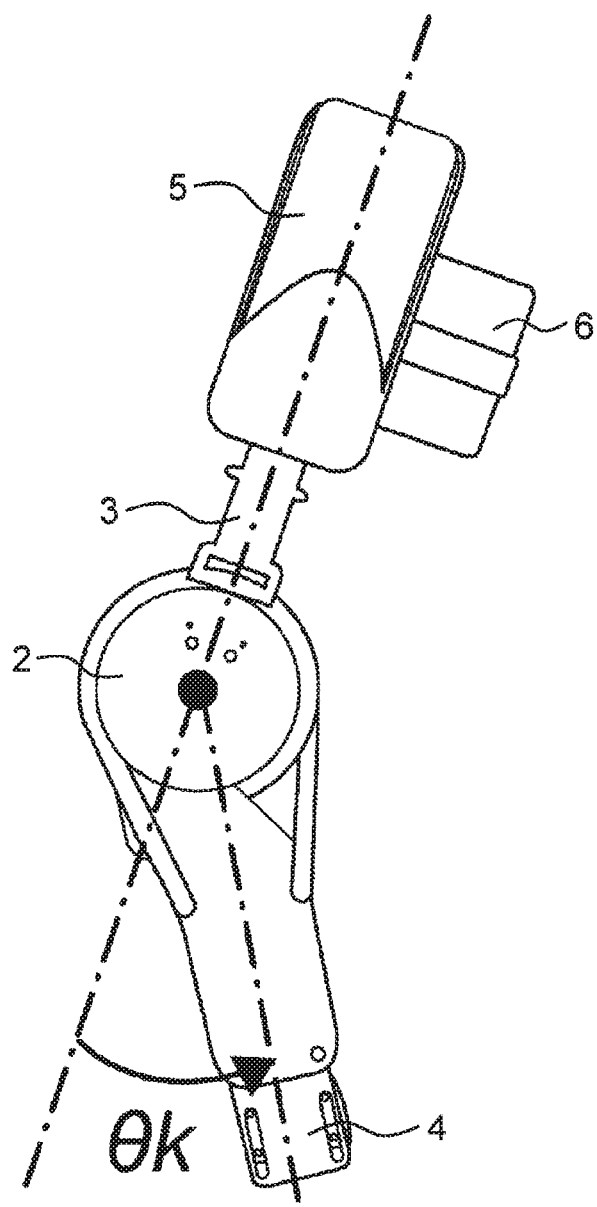
FIG. 7 is a diagram for explaining the knee joint angle.

In this formula (1), $\theta_k$ is the knee joint angle illustrated in FIG. 7 and $\alpha$, $\alpha'$, $\beta$, $\beta'$, and $\beta''$ are parameters for a linear function. $\theta_{t1}$ and $\theta_{t2}$ indicates threshold values for this function.

During the swing leg period, the route is adjusted by referring to a trajectory of the knee joint angle. The knee joint angle to which reference is made is calculated by using a minimum jerk trajectory and the trajectory of the knee joint angle is calculated from the angular velocity and maximum angular position of the knee joint, and an angular position to make the foot part 12 of the trans-femoral prosthesis 10 contact the stair. In this embodiment, the route is expressed as indicated in the following formula (2).

[Math. 2]

$$\theta(t) = \theta_{k0} + \dot{\theta}_{k0} \cdot t_p \cdot t + \{10 \cdot (\theta_t - \theta_{k0}) - 6 \cdot \dot{\theta}_{k0} \cdot t_p\} t^3 + \{-15 \cdot (\theta_t - \theta_{k0}) + 8 \cdot \dot{\theta}_{k0} \cdot t_p\} t^4 + \{6 \cdot (\theta_t - \theta_{k0}) - 3 \cdot \dot{\theta}_{k0} \cdot t_p\} t^5. \quad (2)$$

In this formula (2), $\theta_{k0}$ is an initial knee joint angle and $\dot{\theta}_{k0}$ is an initial knee joint angular velocity. $\theta_t$ is a knee joint angle when the foot part is in contact with the stair and $t_p$ is duration of the swing leg period.

(3-2) Control Method for Stepping Down Stairs

When a healthy person steps down the stairs, concentric contraction occurs during the swing leg period so that the knee joint extends from the flexed position. This concentric contraction is a type of contraction that causes the length of the muscles to shorten and makes an origin and a stop come closer to each other. Then, eccentric contraction occurs during the stance leg period so that the knee joint is slowly flexed from the extended position. This eccentric contraction is a type of contraction that causes the length of the muscles to extend and makes the origin and the stop separated from each other.

Since the above-described torque occurrence direction is the same regardless of the rotational direction, it is unnecessary to divide the phase and the control can be performed in one phase. The torque is expressed as indicated in the following formula (3).

[Math. 3]

$$\tau = k_p(\theta - \theta_{kf}) + k_d \dot{\theta} \quad (3)$$

This formula (3) means that the driving unit 2 supplies torque like a spring or a damper: and $\tau$ represents command torque, $\theta_k$ represents a knee joint angle, $\theta_{kf}$ represents a completely extended angle, $\dot{\theta}$ represents a knee joint angular velocity, and $k_p$ and $k_d$ represent gain control.

Accordingly, the artificial leg motion assisting apparatus 1 according to this embodiment can make it possible to walk in a manner similar to a healthy person by enabling not only walking on the level ground, but also the stair stepping motion by smoothly switching the task in response to the wearer's motion, while estimating the phase of the wearer's task and causing the drive unit to generate the motive power according to the estimated phase.

(4) Stair Stepping Motion Test

An experiment of the wearer's actual walking was conducted by attaching the artificial leg motion assisting apparatus 1 according to this embodiment to a commercially-available trans-femoral prosthesis (3R80+ by Ottobock). In this experiment, in order for a healthy person to wear a trans-femoral prosthesis, the trans-femoral prosthesis 10 which is secured to and retained at a bypass artificial leg for retaining a target leg in a flexed state is applied by using the bypass device as a dummy thigh socket.

In this test, the healthy person was 173 cm tall and weighed 83 kg and performed a motion to step up five-step stairs and a motion to step down the five-step stairs alternately. Incidentally, regarding the size of the stairs, the rise (height) of each step was 12.4 cm, its step surface was 27.2 cm, and its width was 92.5 cm.

In this test, average values and standard deviations regarding the knee joint angle, the knee joint torque, and the ground reaction force on the front foot part (toe part) side and the rear foot part (heel part) side were calculated for the stair-stepping-up motion and the stair-stepping-down motion. All necessary parameters for the calculation were adjusted to suit the subject in order to implement the stair-stepping-up motion and the stair-stepping-down motion.

Figure 8:
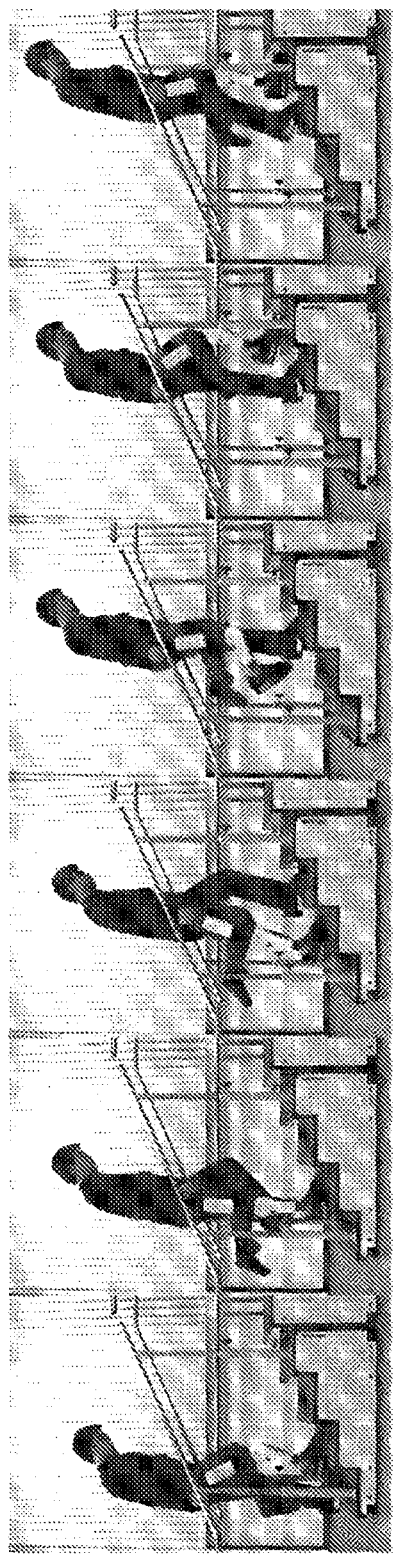
FIG. 8 is a diagram for explaining a motion process when implementing a stair-stepping-up motion.

FIG. 8 illustrates a motion process for the healthy person to perform the stair-stepping-up motion with their one leg in a physically disabled state in a manner similar to an above knee amputee and by using the bypass device after the artificial leg motion assisting apparatus 1 according to this embodiment was mounted on that one leg.

Figure 9:
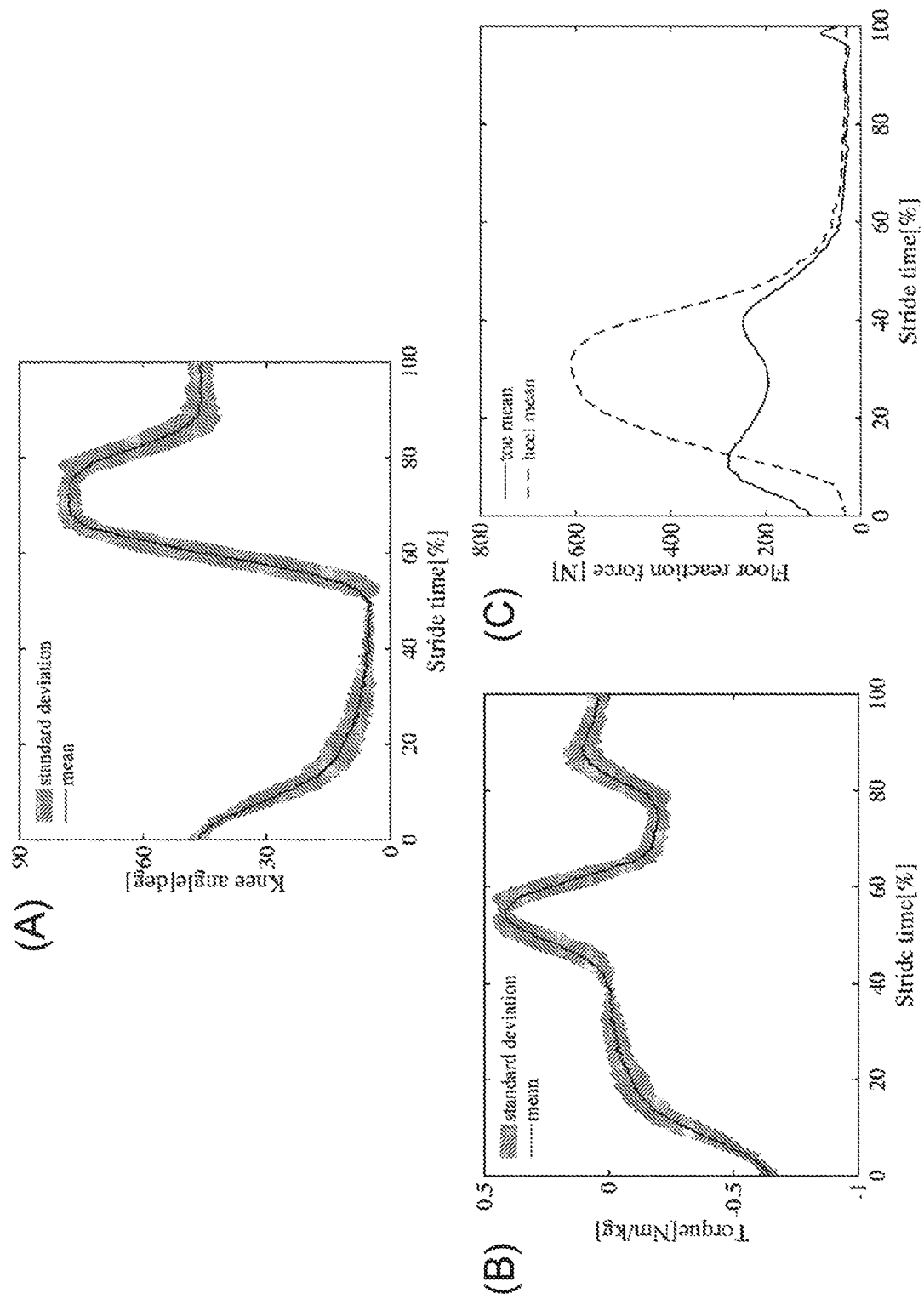
FIG. 9 is a diagram illustrating the knee joint angle, knee joint torque, and ground reaction force after torque normalization.

FIG. 9 illustrates the knee joint angle (FIG. 9A), the knee joint torque (FIG. 9B), and the ground reaction force on the front foot part (toe part) side and the rear foot part (heel part) side (FIG. 9C) between the stair-stepping-up motions after normalization of the torque.

Average time required for one step was 1.70 s and a standard deviation was 0.10 s. An average maximum angle of the knee joint was 78.2 degrees, a minimum angle was 4.8 degrees, maximum torque to extend the knee joint was 0.641 nm/kg, and maximum torque to flex the knee joint was 0.417 nm/kg.

According to the stair-stepping-up motion test, the torque generated for extension reached the maximum value when the phase changed to the stance leg period. At the same moment, the knee joint started to extend. Then, the knee joint angle reached the completely extended angle. The torque for flexion started to be generated when the phase changed to the swing leg period. After the phase changed to the swing leg period, the torque reached the maximum value. Subsequently, the knee joint angle reached its maximum value. Consequently, it was generally confirmed that even when wearing the artificial leg motion assisting apparatus 1, the stair-stepping-up motion can be performed in a stepped manner in the same way as a healthy person does.

Figure 10:
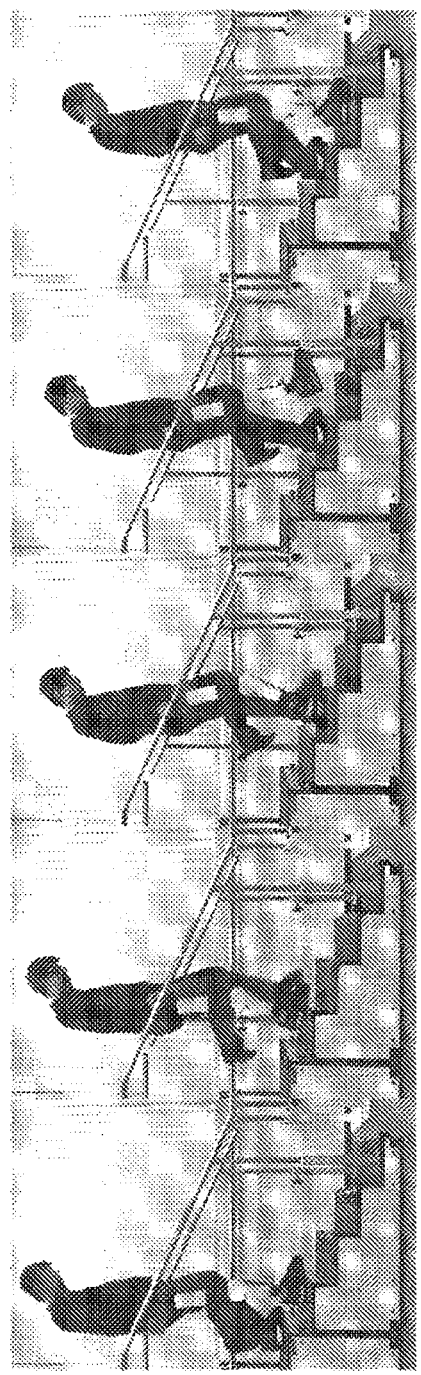
FIG. 10 is a diagram for explaining a motion process when implementing a stair-stepping-down motion.

FIG. 10 illustrates a motion process for the healthy person to perform the stair-stepping-down motion with their one leg in a physically disabled state in a manner similar to an above knee amputee by using the bypass device after the artificial leg motion assisting apparatus 1 according to this embodiment was mounted on that one leg.

Figure 11:
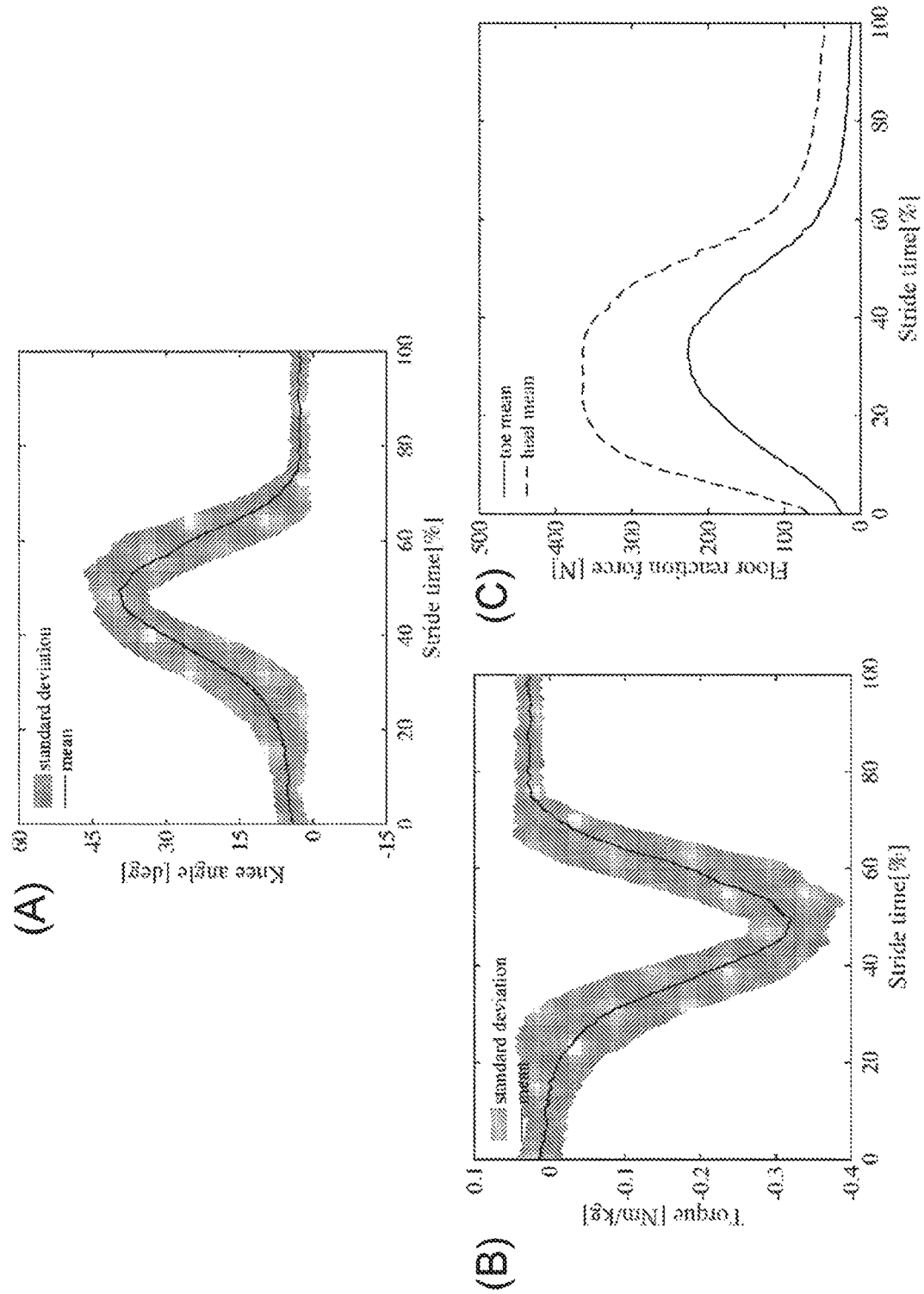
FIG. 11 is a diagram illustrating the knee joint angle, knee joint torque, and ground reaction force after the torque normalization.

FIG. 11 illustrates the knee joint angle (FIG. 11A), the knee joint torque (FIG. 11B), and the ground reaction force on the front foot part (toe part) side and the rear foot part (heel part) side (FIG. 11C) between the stair-stepping-down motions after normalization of the torque.

Average time required for one step was 1.28 s and a standard deviation was 0.13 s. An average maximum angle of the knee joint was 39.6 degrees, a minimum angle was 2.3 degrees, maximum torque to extend the knee joint was 0.031 nm/kg, and maximum torque to flex the knee joint was 0.321 nm/kg.

According to the stair-stepping-down motion test, the knee joint started to be flexed when the foot part contacted the stair. The torque generated for flexion reached the maximum value when the knee joint angle reached the maximum angle. The knee joint started to be extended when the foot part moved away from the stair. Then, the knee joint angle reached the completely extended angle. It was generally confirmed that even when wearing the artificial leg motion assisting apparatus 1, the stair-stepping-down motion can be performed in a stepped manner in the same way as a healthy person does.

(5) Obstacle-Striding Test

Regarding the present invention, a test for passing through a route by striding an obstacle (a striding test) was conducted in addition to the above-described stair-stepping motion tests; and it was confirmed by measuring the respective sensor values including the biological potential signal before and after a striding motion that the artificial leg motion assisting apparatus 1 can be operated voluntarily and its voluntary motion makes it possible to perform the motion which is difficult for the artificial leg to perform.

Figure 12:
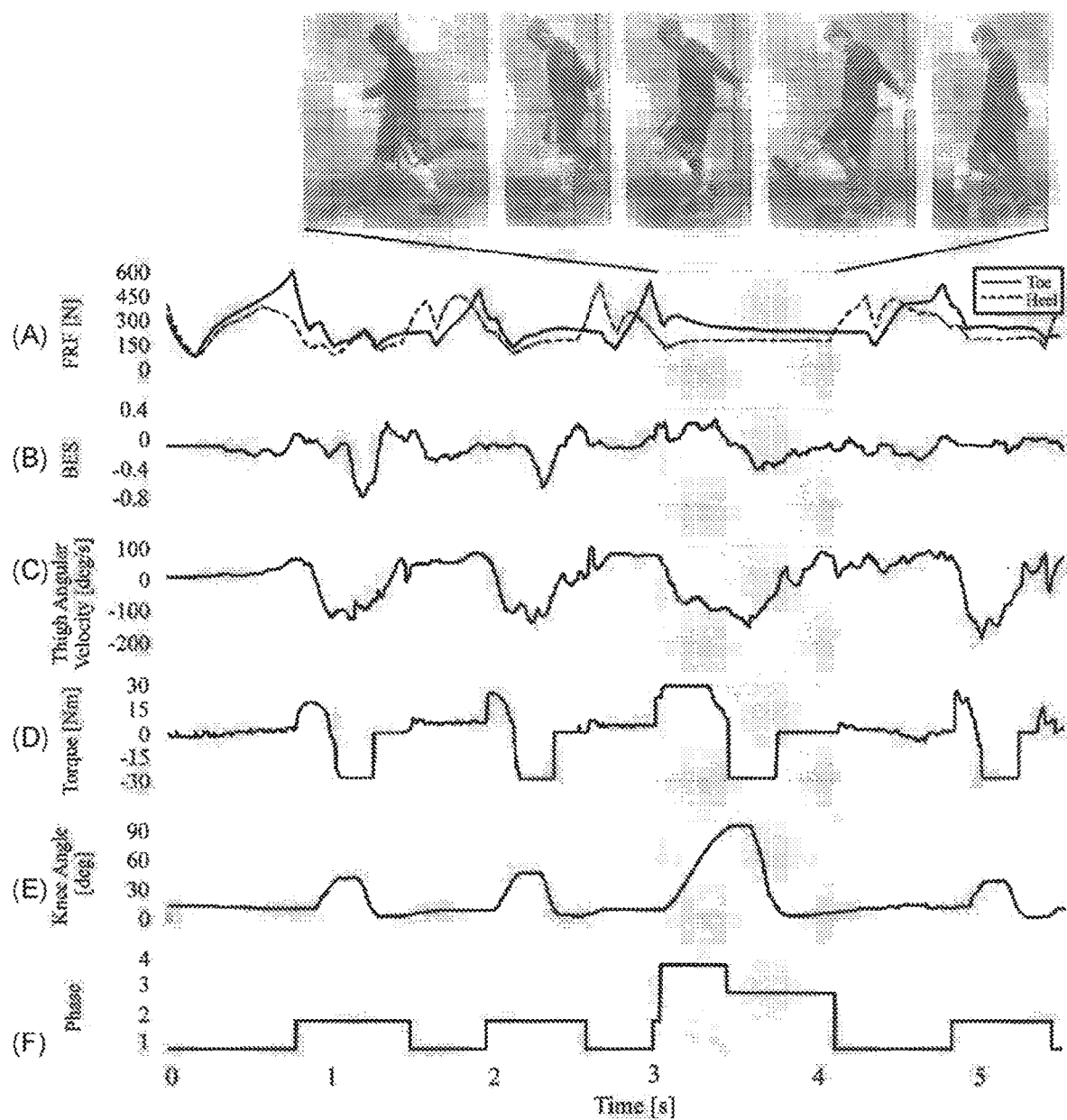
FIG. 12 is a timing chart for explaining walking control of an obstacle-striding test.

FIG. 12 illustrates a timing chart for explaining walking control for the obstacle-striding test. The biological potential signal is a value obtained by performing normalization based on a value upon 100% MVC (FIG. 12B). Characteristic changes in the ground reaction force and the thigh angular velocity can be observed for every step (FIG. 12A and FIG. 12C). The phase during walking is switched properly according to the walking control (FIG. 12F). It can be confirmed that the knee joint is largely flexed as compared to during walking when the intention of motion was detected (FIG. 12(E)).

(6) Other Embodiments

This embodiment has described the case where the artificial leg motion assisting apparatus 1 having the structure in which the drive unit (actuator) for the driving unit is driven to rotate between the thigh frame and the lower leg frame; however, the present invention is not limited to this example and the driving output of the actuator may be linear reciprocating motions of a cylinder so that the thigh frame and the lower leg frame can be made movable relatively to each other.

Figure 13:
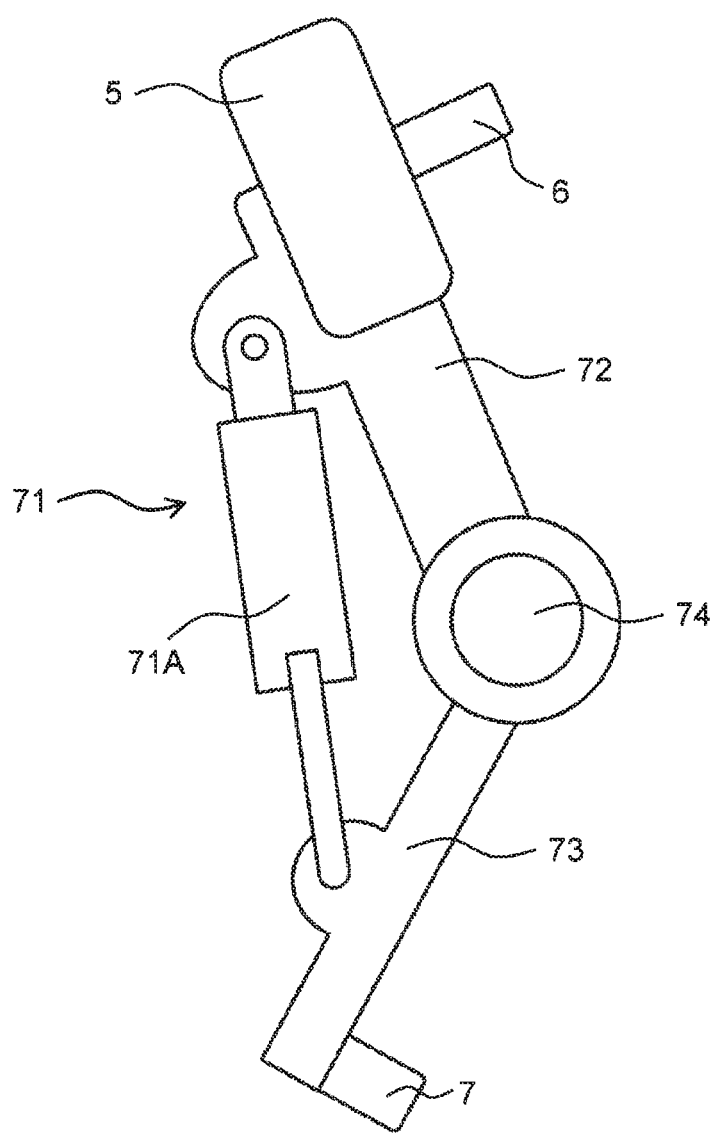
FIG. 13 is an outside drawing illustrating an overall configuration of an artificial leg motion assisting apparatus according to another embodiment.

Specifically speaking, for example, with an artificial leg motion assisting apparatus 70 as illustrated in FIG. 13, a driving unit 71 is composed of a cylinder 71A of a hydraulic type, a pneumatic type, a linear motor type, or the like. A thigh frame 72 and a lower leg frame 73 are coupled in a freely movable manner to one end and the other end of the cylinder 71A, respectively, and the thigh frame 72 and the lower leg frame 73 are coupled to each other in a freely rotatable manner via a joint movable part 74.

The control apparatus 5 (FIG. 4) for controlling driving of the actuator and a power supply battery (not shown in the drawing) are attached to the outside of the thigh frame 72 and the thigh socket cuff (fastening member) 6 is connected to the inside of the thigh frame 72. The lower leg connection ring (holding member) 7 is connected to the inside lower end of the frame body of the lower leg frame 73.

This artificial leg motion assisting apparatus 70 makes it possible to make the thigh frame 72 and the lower leg frame 73 relatively movable around the joint movable part 74 as the rotation center by transforming the driving output of the drive unit (actuator) in the driving unit 71 to the linear reciprocating motions of the cylinder 71A.

REFERENCE SIGNS LIST 1, 70: artificial leg motion assisting apparatus
2, 71: driving unit
3, 72: thigh frame
4, 73: lower leg frame
5: control apparatus
6: thigh socket cuff
7: lower leg connection ring
8: insole
10: trans-femoral prosthesis
11: thigh socket
12: foot part
13: lower leg support pole
14: knee joint coupling
20: data storage unit
21: drive unit
22: knee joint angle sensor
23: absolute angle sensor
24: biological signal detection unit
25: interaction moment sensor
26: vibration sensor
27: laser range sensor
28: RGB-D sensor
29: 3-dimensional depth image sensor
30: sound concentrating microphone
31: GRF sensor
32: GRF control unit
33: transmitter
40: receiver
50: driving torque estimation unit
51: joint torque estimation unit
52: joint shaft torque estimation unit
53: data input unit
54: parameter estimation unit
55: control unit
56: calibration unit
57: data output unit
58: power amplification unit
74: joint movable part

The invention claimed is:

1. A wearable-type artificial leg motion assisting apparatus provided separately from a trans-femoral prosthesis including a knee joint coupling for rotatably coupling a thigh socket for housing an above knee amputated end of a wearer to a lower leg support pole engaged with a foot part, the artificial leg motion assisting apparatus supporting a rotational motion of the knee joint coupling, the artificial leg motion assisting apparatus comprising:
a thigh frame fastened to the thigh socket via a fastening member;
a lower leg frame movably retained at the lower leg support pole via a holding member;
a drive unit that is coupled to the thigh frame and the lower leg frame and drives actively or passively in conjunction with a thigh motion of the wearer;
a biological signal detection unit that detects an electrical potential as a biological signal generated in association with the thigh motion of the wearer;
a control unit that causes the drive unit to generate motive power according to an intention of the wearer on the basis of the biological signal acquired by the biological signal detection unit;
a coupling's physical amount detection unit that detects a physical amount as a joint moment of the knee joint coupling in association with the thigh motion of the wearer on the basis of an output signal from the drive unit;
a leg motion monitoring unit which is provided on the trans-femoral prosthesis and monitors a motion of a leg part where the trans-femoral prosthesis is not mounted;
a parameter estimation unit that estimates a kinetic parameter specific to the trans-femoral prosthesis on the basis of a result of the detection measured within a specified amount of time by the coupling's physical amount detection unit and a result of the monitoring by the leg motion monitoring unit; and
an impedance adjustment unit that adjusts mechanical impedance specific to the knee joint coupling on the basis of the kinetic parameter estimated by the parameter estimation unit,
wherein the control unit controls the drive unit by a specified control method on the basis of the mechanical impedance adjusted by the impedance adjustment unit.

2. The artificial leg motion assisting apparatus according to claim 1,
wherein a leg motion monitoring unit which is provided on the trans-femoral prosthesis and monitors a motion of a leg part where the trans-femoral prosthesis is not mounted, and the parameter estimation unit estimates the kinetic parameter of the trans-femoral prosthesis on the basis of a result of the detection by the coupling's physical amount detection unit and a result of the monitoring by the leg motion monitoring unit.

3. The artificial leg motion assisting apparatus according to claim 1,
comprising a sound concentrating microphone that is provided on the foot part of the trans-femoral prosthesis and collects a walking sound of the trans-femoral prosthesis,
wherein the parameter estimation unit modifies the estimated kinetic parameter of the trans-femoral prosthesis on the basis of the walking sound collected by the sound concentrating microphone.

4. The artificial leg motion assisting apparatus according to claim 1,
comprising a vibration detection unit that is provided on the lower leg frame of the trans-femoral prosthesis and detects vibrations from a floor face during walking,
wherein the parameter estimation unit modifies the estimated kinetic parameter of the trans-femoral prosthesis on the basis of the vibrations detected by the vibration detection unit.

5. The artificial leg motion assisting apparatus according to claim 1,
comprising:
a thigh angle sensor that is provided on the thigh frame and detects a thigh angle determined between a thigh direction and a vertical direction;
a knee joint angle sensor that is provided on the drive unit and detects an angle and angular velocity of the knee joint coupling;
a ground reaction force sensor that is provided on the foot part and detects a ground reaction force to the wearer; and
a data storage unit that stores a plurality of reference parameters representing a series of minimum motion units (phases) constituting motion patterns of the wearer which are classified as tasks,
wherein the control unit estimates a phase of a task for the wearer by comparing the thigh angle, the knee joint angle, and the ground reaction force with the respective reference parameters stored in the data storage unit and then causes the drive unit to generate motive power according to the estimated phase.

6. A method for controlling a wearable-type artificial leg motion assisting apparatus provided separately from a trans-femoral prosthesis including a knee joint coupling for rotatably coupling a thigh socket for housing an above knee amputated end of a wearer to a lower leg support pole engaged with a foot part, the artificial leg motion assisting method supporting a rotational motion of the knee joint coupling,
the artificial leg motion assisting method comprising:
a first step of detecting an electrical potential as a biological signal generated in association with a thigh motion of the wearer;
a second step of causing a drive unit, which is coupled to a thigh frame fastened to the thigh socket via a fastening member and to a lower leg frame movably retained at the lower leg support pole via a holding member and which drives actively or passively in conjunction with the thigh motion of the wearer, to generate motive power according to an intention of the wearer on the basis of the biological signal acquired in the first step;
a third step of detecting a physical amount as a joint moment of the knee joint coupling in association with the thigh motion of the wearer on the basis of an output signal from the drive unit, and monitoring of a motion of a leg part where the trans-femoral prosthesis is not mounted;
a fourth step of estimating a kinetic parameter specific to the trans-femoral prosthesis on the basis of a result of the detection of the physical amount of the knee joint coupling in association with the thigh motion of the wearer measured within a specified amount of time and a result of the monitoring of the motion of the leg part where the trans-femoral prosthesis is not mounted in the third step;
a fifth step of adjusting mechanical impedance specific to the knee joint coupling on the basis of the kinetic parameter estimated in the fourth step; and
a sixth step of controlling the drive unit by a specified control method on the basis of the mechanical impedance adjusted in the fifth step.

7. The artificial leg motion assisting method according to claim 6,
wherein in the fourth step, the kinetic parameter of the trans-femoral prosthesis is estimated on the basis of a result of the detection by the coupling's physical amount detection unit and a result of monitoring of a motion of a leg part where the trans-femoral prosthesis is not mounted.

8. The artificial leg motion assisting method according to claim 6,
wherein in the fourth step, the estimated kinetic parameter of the trans-femoral prosthesis is modified on the basis of the walking sound collected via a microphone provided on the foot part of the trans-femoral prosthesis.

9. The artificial leg motion assisting method according to claim 6,
wherein in the fourth step, the estimated kinetic parameter of the trans-femoral prosthesis is modified on the basis of a result of detection of vibrations from a floor face during walking as detected from the lower leg frame of the trans-femoral prosthesis.

10. The artificial leg motion assisting method according to claim 6,
wherein a plurality of reference parameters representing a series of minimum motion units (phases) constituting motion patterns of the wearer which are classified as tasks are stored in a data storage unit; and
wherein in the sixth step, a phase of a task for the wearer is estimated by comparing a thigh angle determined between a thigh direction and a vertical direction, an angle and angular velocity of the knee joint coupling, and a ground reaction force to the wearer with the respective reference parameters stored in the data storage unit and then the drive unit is caused to generate motive power according to the estimated phase.

* * * * *